United States Patent
Assmann et al.

(10) Patent No.: US 8,110,160 B2
(45) Date of Patent: Feb. 7, 2012

(54) CUVETTE

(75) Inventors: Frank Assmann, Magdeburg (DE); Christa Dumschat, Barleben (DE); Berthold Walter, Niederndodeleben (DE); Guenter Gabriel, Magdeburg (DE)

(73) Assignee: EKF—Diagnostic GmbH, Barleben (DE)

( * ) Notice: Subject to any disclaimer, the term of this patent is extended or adjusted under 35 U.S.C. 154(b) by 480 days.

(21) Appl. No.: 12/302,652

(22) PCT Filed: May 30, 2007

(86) PCT No.: PCT/DE2007/000979
§ 371 (c)(1),
(2), (4) Date: Nov. 26, 2008

(87) PCT Pub. No.: WO2007/137572
PCT Pub. Date: Dec. 6, 2007

(65) Prior Publication Data
US 2009/0185957 A1  Jul. 23, 2009

(30) Foreign Application Priority Data
May 30, 2006  (DE) .................. 10 2006 025 477

(51) Int. Cl.
G01N 21/00 (2006.01)
G01N 21/75 (2006.01)
(52) U.S. Cl. ..................... 422/554; 422/425
(58) Field of Classification Search .................. 422/554, 422/425
See application file for complete search history.

(56) References Cited

U.S. PATENT DOCUMENTS

| | | | |
|---|---|---|---|
| 3,705,000 A | 12/1972 | Guerra | |
| 4,088,448 A | 5/1978 | Lilja et al. | |
| 4,171,866 A | 10/1979 | Tolles | |
| 5,674,457 A * | 10/1997 | Williamsson et al. | 422/554 |
| 6,207,000 B1 | 3/2001 | Schwobel et al. | |
| 7,833,479 B2 * | 11/2010 | Therup et al. | 422/72 |
| 2003/0007893 A1* | 1/2003 | Purcell | 422/58 |
| 2004/0028558 A1* | 2/2004 | Pollock et al. | 422/57 |

FOREIGN PATENT DOCUMENTS

| | | |
|---|---|---|
| DE | 19753850 A1 | 6/1999 |
| DE | 19810499 | 9/1999 |
| EP | 0 487 068 A1 | 11/1991 |
| EP | 0 803 288 A2 | 4/1997 |
| EP | 0 821 784 B1 | 11/1998 |
| EP | 1 096 254 A2 | 10/2000 |
| EP | 1 389 443 A1 | 2/2004 |
| GB | 2 090 659 A | 7/1982 |
| GB | 2 341 925 A | 9/1999 |
| WO | WO 96/33399 | 10/1996 |
| WO | WO 99/30158 | 6/1999 |
| WO | WO 2005/043134 A1 | 10/2004 |
| WO | WO 2005/119211 | 6/2005 |

* cited by examiner

Primary Examiner — Lore Jarrett
(74) Attorney, Agent, or Firm — Whitham Curtis Christofferson & Cook, PC

(57) ABSTRACT

Disclosed is a cuvette for taking a measurement on a liquid, comprising a monolithic cuvette body with a cavity (4) in the form of a narrow gap that is formed between two at least approximately parallel wall surfaces (15, 16) and is delimited by an inner wall (5, 6, 11) and a drawing edge (2) which is open towards the surroundings and from which the liquid is drawn into the cavity (4) forming a measurement zone (13) under the effect of a capillary force.

21 Claims, 1 Drawing Sheet

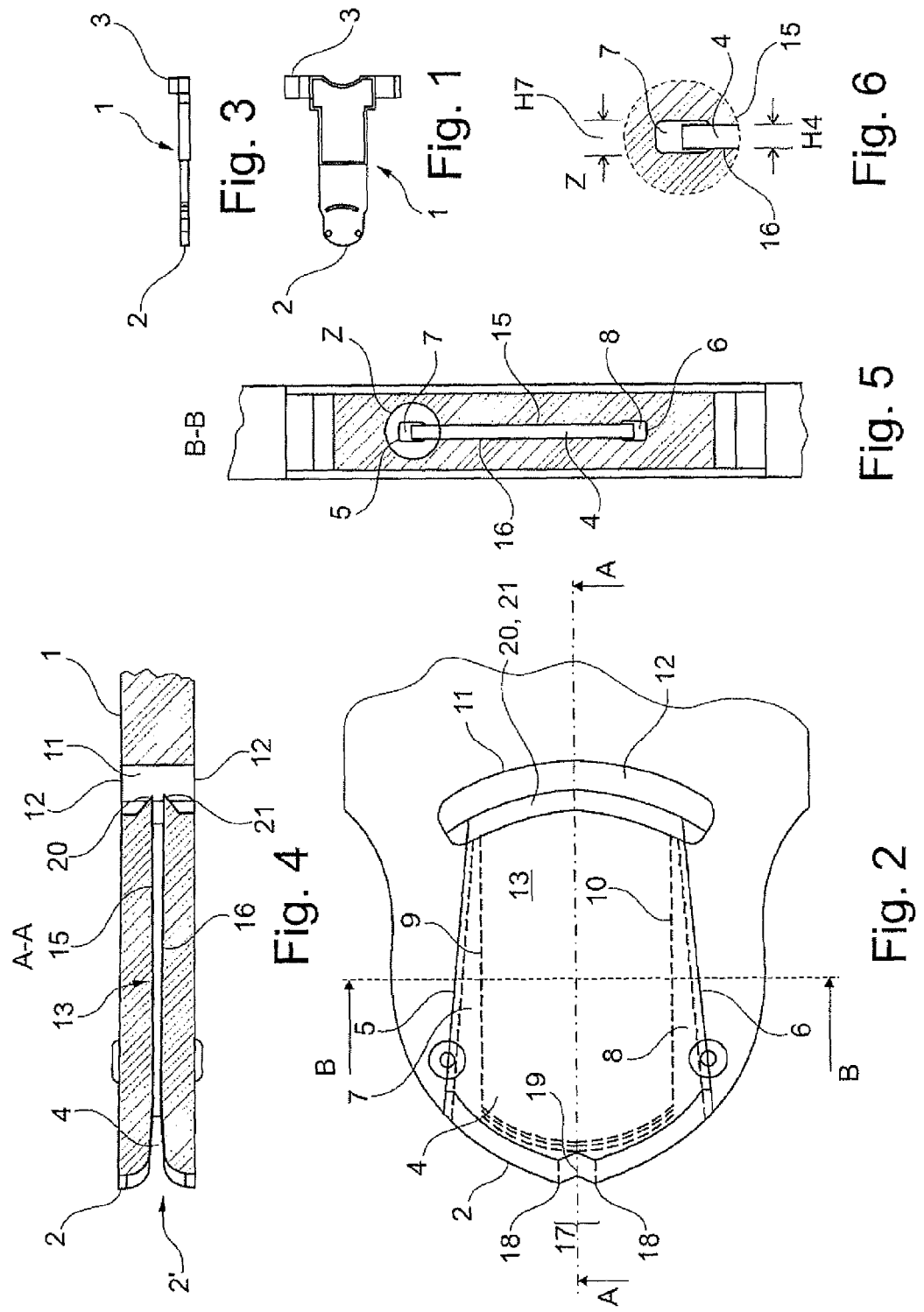

CUVETTE

The invention relates to a cuvette for taking a measurement of a liquid, having a cuvette body with a cavity in the form of a narrow slot which, when the cuvette body is made by injection molding, is formed by means of an insert and is created between two at least approximately parallel wall surfaces and is delimited by an inner wall and by a drawing edge which is open to the outside and from which, by capillary action, the liquid is drawn into the cavity, which forms a measuring region, wherein the cuvette body has a longitudinal axis, and the inner wall has longitudinal wall sections that extend from the drawing edge and an end region that connects the longitudinal wall sections, and is coated with a chemical reagent that is applied in the wet state and is then dried as a result of the evaporation of gases being transported out of the cavity.

A cuvette of this kind is known from EP 0 821 784 B1. The slot that forms the cavity is made in a rectangular cuvette body that is made in one piece in the form of a strip and terminates in asymmetrical manner by the open drawing edge of the cavity such that an acute-angled corner that serves as the drawing region for a drop of blood is created. The inner walls of the cuvette are coated with a chemical reagent, as a result of which for example hemoglobin, a substance contained in blood, undergoes a chemical coloring reaction. As a result of measuring transmission through the wall surfaces within the measuring region, it is thus possible to determine the quantity of hemoglobin contained in the blood.

[ . . . ] inner wall is preferably drawn by suction into the cavity by a capillary action such that the measuring region, which is approximately circular in form, fills from the margin inward. The inner wall merges from an inlet longitudinal wall section by way of an arcuate section of the measuring region into an outlet longitudinal wall section that is at an acute angle in relation to the inlet longitudinal wall section and, because of the asymmetrical form of the end of the cuvette, is substantially shorter than the inlet longitudinal wall section. To promote the flow profile that is sought, the height of the slot is reduced, by means of a channel region of the inner wall in step-shaped or conically tapering form, by comparison with the height of the slot of the cavity in the measuring region. This is intended to bring about a greater capillary action in a channel that adjoins the inner wall.

U.S. Pat. No. 4,088,448 discloses a cuvette that is also made in a rectangular base body that is in the form of a strip. The cavity, which is formed by a slot in the base body, is formed symmetrically in the longitudinal direction of the base body, and has two longitudinal wall sections that taper toward one another and are connected to the inner wall by an end wall section that extends transversely in relation to the longitudinal axis. In practice, drawing a drop of blood into the cavity is performed by way of a corner of the strip-form base body on which the short open drawing edge is located. Because the cavity is in a form that tapers symmetrically, air is frequently included in the closed end of the cavity as a result of its being insufficiently filled. In a variant, the cavity is located in the center of the strip-form base body, and has two drawing channels, each of which extends as far as the short edge, in the longitudinal direction of the cuvette. A construction of this kind is neither practical to handle nor economic to make.

One problem of the known, one-piece cuvettes is that the wall surfaces are frequently not coated with the chemical reagent evenly. Conventionally, the reagent is applied by filling the cavity with the dissolved reagent and depositing the reagent on the wall surfaces of the cavity in a drying process that is intensified by the addition of heat. During this, a reduced film thickness of reagent is achieved in particular at the margin of the cavity.

Insufficient coating with reagent results in falsification of the measurement result if the measurement is performed over the entire measuring region, because in this case a reduced coating at the margins of the measuring region has an effect on the measurement. Moreover, coating with the chemical reagent has an effect on the wetting of the wall surface with liquid, such that the liquid is not drawn evenly into the cavity by the capillary action if the coating of reagent has not been applied evenly.

The object of the invention is therefore to provide a cuvette of the type mentioned at the outset such that its cavity is completely and evenly filled with the liquid by capillary action and error-free measurement is obtained because the cuvette can be evenly coated with the chemical reagent.

According to the invention, this object is achieved by a cuvette of the type mentioned at the outset that is characterized in that the drawing edge has a drawing region at a spacing from the longitudinal wall sections, in that the longitudinal wall sections extend at a spacing on either side of a center axis of drawing that runs centrally from the drawing region to the end region, in that the end region has an opening to the outside, and in that marginal regions are formed along the longitudinal wall sections and form therein a greater spacing between delimiting surfaces than the spacing between the adjacent parallel wall surfaces.

In the present cuvette, the asymmetric shape, which is recognized as optimized, of the cavity and the inner wall, through which the liquid is drawn into the cavity at a longitudinal wall section, is deflected at the margin of the measuring region and is then guided back to the open drawing edge by way of a short longitudinal wall section, is abandoned. Rather, the cuvette according to the invention provides for the liquid to be drawn in approximately centrally at the drawing edge for complete filling of the cavity, and indeed to migrate to the end region by way of a central slot as a result of capillary action. If air is included during this, it can escape to the outside through the opening in the end region, that is to say beyond the measuring region. Here, the opening may be constructed such that no liquid comes out of the cuvette through the opening.

The marginal regions that are provided along the longitudinal wall sections on either side of the drawing direction and that have a greater wall spacing between the two delimiting surfaces parallel to the wall surfaces, result in a reduced capillary action in the marginal regions, with the result that the cavity is filled more quickly in the central region of the cavity and a flow front that is formed is farther back toward the marginal regions, because the flow rate in the marginal regions is slower because of the reduced capillary action. The spacing between the delimiting surfaces of the marginal regions is advantageously at least 20 µm, preferably at least 50 µm, particularly preferably at least 100 µm greater than the spacing between the adjacent parallel wall surfaces. The marginal regions that are formed according to the invention have the result that coating of the wall surfaces of the cavity of the one-piece cuvette body outside the marginal regions is substantially more even than was the case with the conventional shapes of cuvette. When the chemical reagent is applied in the wet state and then dried, the marginal regions having a greater cross section in the direction of height produce accelerated transport of the evaporated gases out of the cavity, as a result of which it becomes possible to form an even film by drying outside the marginal regions. Because the measuring region is located between the marginal regions, the measuring region can be coated evenly with the chemical reagent.

Because of the function of the cuvette that has been described, the drawing region preferably lies centrally on the open drawing edge. Drawing in the liquid, for example a drop of blood, does not therefore take place in the region of a longitudinal wall section—as was the case hitherto—but in a manner spaced between the longitudinal wall sections, as a result of which a flow profile that is independent of the longitudinal wall sections is produced.

This feature is supported by the fact that in a preferred embodiment of the invention the drawing region is formed to jut forward in relation to the rest of the region of the drawing edge. In this way, drawing in of the liquid in the central drawing region is supported.

The drawing region can in this case be formed by the two wall surfaces at the open drawing edge being constructed to have two forwardly jutting projections with a central cutout. Here, the central cutout can include the approximately triangular notch.

In a preferred embodiment of the invention, the longitudinal axis of the cuvette extends through the drawing region, preferably with the drawing center axis and the longitudinal axis at least approximately coinciding.

The marginal regions, which are formed to have a greater height, preferably merge into the end region. They may extend toward one another in a direction oblique in relation to the drawing direction, to support the formation of an even, approximately parabolic flow front. Here, it may be advantageous for the width of the marginal regions to diminish toward the end region and for the marginal regions—like the longitudinal wall sections—to be rectilinear.

The end region preferably adjoins the marginal regions in a manner extending transversely in relation thereto.

For adaptation to the flow front, it may be advantageous for the end region to be of curved form and in particular [ . . . ] the shape of a [ . . . ] end region to communicate with the outside, may preferably extend over its entire length. It is further preferable if the opening of the end region is formed in both the wall surfaces that delimit the end region.

An embodiment of the invention that reliably prevents liquid from coming out of the opening of the end region provides for the slot of the cavity to extend by means of its wall surfaces into the end region, with wall portions that are reduced in height. In particular, the wall portions that project into the end region may have edges that taper to a point. This produces a large cross sectional surface of flow for the air that is pushed out of the cavity by the liquid, while on the other hand the free cross section for the liquid, which has a certain surface tension, is reduced such that the liquid cannot come out because of its surface tension.

The invention will be explained in more detail below with reference to an exemplary embodiment, which is illustrated in the drawing, in which:

FIG. 1 shows a plan view of an embodiment of a cuvette according to the invention;

FIG. 2 shows a detail Y of the plan view according to FIG. 1, in an enlarged illustration;

FIG. 3 shows a side view of the cuvette according to FIG. 1;

FIG. 4 shows a detail X according to FIG. 3 in a section along the line A-A from FIG. 1;

FIG. 5 shows a cross section along the line B-B in FIG. 2; and

FIG. 6 shows a detail Z from FIG. 5, in an enlarged illustration.

The cuvette illustrated in FIG. 1 has an elongate and substantially rectangular cuvette body 1 that is made in one piece by injection molding and is formed such that it has an open drawing edge 2 at one end and handling attachments 3 at the opposing end.

The enlarged illustration in FIG. 2 shows that the housing body 1 has, at the end with the drawing edge 2, a cavity 4 in the form of a slot that is open toward the drawing edge 4. The width of the cavity 4 is delimited by two longitudinal wall sections 5, 6 that extend from the drawing edge 2 approximately in the longitudinal direction (cf. line of section A-A in FIG. 2) of the housing body 1. In this arrangement, the two longitudinal wall sections 5, 6 run obliquely from the drawing edge 2 and somewhat toward one another. A respective marginal region 7, 8 adjoins each of the two rectilinear longitudinal wall sections 5, 6, and the width of these marginal regions diminishes, starting from the drawing edge 2, such that an edge 9, 10 that is remote from the longitudinal wall section 5, 6 runs parallel to the longitudinal axis of the housing body 1. The marginal regions 7, 8 open into an end region 11, which is curved into an arcuate section.

As is clear from FIG. 4, the end region 11 forms, over its entire length, a slot-shaped opening 12 on the upper side and underside of the housing body 1 (as seen in the view of FIG. 1).

Approximately centrally between the drawing edge 2 and the end region 11, there is a measuring region 13, which includes a polished surface of the housing body 1, which is formed from a transparent material.

As is clear from FIG. 4, the cavity 4 is formed by a longitudinal slot that is delimited by an upper wall surface 15 and, running approximately parallel thereto, a lower wall surface 16. In the measuring region 13 the two wall surfaces 15, 16 are at a small spacing from one another that increases slightly toward the drawing slot 2 in order to make it possible to remove from the mold a sliding element that forms the slot for the one-piece housing body 1 in an injection molding process, using conventional technology.

As is clear from FIG. 2, the drawing edge 2 extends on either side of the longitudinal axis of the housing body 1 and forms a drawing region 17 that forms at the part of the rounded drawing edge 2 that juts farthest forward. The drawing region is provided with two projections 18 that have a notch-shaped cutout 19 between them. In the illustrated exemplary embodiment, the notch-shaped cutout 19 lies along the longitudinal axis of the housing body 1.

The cavity 4 that is formed by the slot extends from the drawing edge 2 to the end region 11, which lies beyond the measuring region 13. In the end region 11, the wall portions 20, 21 that form wall surfaces 15, 16 for the wall surfaces 15, 16 are prolonged substantially in a straight line, whereas they project into the end region 11 by means of beveled outer sides so that they form a point of diminishing wall thickness.

The axial length of the end region 11 is for example 1 mm. As a result of the wall portions 20, 21 that project into the end region 11, together with the small slot height between the wall portions 20, 21 and the pointed formation of the ends of the wall portions 20, 21, the liquid, preferably blood, remains in the cavity 4 and cannot leave the housing body 1 through the opening 12 without the action of an external force.

It is clear from the cross sectional illustration in FIG. 5 that the marginal regions 7, 8 along the longitudinal wall sections 5, 6 resemble channels in form and are greater in height than the cavity 4 in the measuring region 13. The enlarged illustration of FIG. 6 shows a height H4 of the cavity 4 in the measuring region 13 that is significantly smaller than a height H7 of the marginal region 7.

The height H4 is in the order of between 0.12 and 0.18 mm, while the height H7 of the marginal region 7 is at least 50 µm, preferably more than 100 µm, greater and is for example between 0.25 and 0.35 mm in size.

To illustrate the order of magnitude of the height of the cavity 4, various height measurements are specified with reference to the longitudinal section of FIG. 4. The cavity 4 has its smallest height toward the end region 11. The height beyond the measuring region 13 is for example 0.12 mm. In the center of the measuring region 13, the height may for example be 0.15 mm, whereas the height at the start of the measuring region 13 may be 0.18 mm. As seen from the drawing slot 2', a height before the measuring region 13 may measure 0.20 mm.

To make it easier to draw in a drop of blood, the drawing slot 2' is given a height of for example 0.35 mm.

The illustrated cuvette results in all the inner walls of the cavity 4 being coated, with any irregularities in the coating occurring in the channel-like marginal regions 7, 8, whereas an even coating is provided in the entire measuring region 13; thus, a quantitatively uniform reaction with the liquid that is drawn in takes place. Because of the even coating of the cavity 4 between the marginal regions 7, 8, an even capillary action is also achieved in the entire region of the cavity 4—between the marginal regions 7, 8—in order to draw the liquid into the cavity 4.

The invention claimed is:

1. A cuvette for taking a measurement of a liquid, comprising
   a one-piece cuvette body having a longitudinal axis and a cavity in the form of a narrow slot, said slot being defined by two at least approximately parallel wall surfaces
   a measuring region formed by the cavity,
   a drawing edge open to the outside of the cavity and adapted to draw liquid into the cavity by capillary action,
   an inner wall delimiting the cavity and having longitudinal wall sections starting from the drawing edge,
   an end region that connects the longitudinal wall sections, and
   a coating of the cavity with a chemical reagent of the kind that is applied in the wet state and then dried as a result of gases evaporating out of the cavity,
wherein
a drawing section of said drawing edge is positioned at a spacing from the longitudinal wall sections,
the longitudinal wall sections extend distant from either side of a flow center axis running centrally from the drawing edge to the end region,
the end region has an opening to the outside, and
marginal regions are formed along the longitudinal wall sections and have a spacing between delimiting surfaces which is greater than the spacing between the adjacent parallel wall surfaces.

2. The cuvette of claim 1, wherein the drawing region lies centrally on the open drawing edge.

3. The cuvette of claim 1, wherein the drawing region juts forward over the rest of the drawing edge.

4. The cuvette of claim 3, wherein the drawing region comprises two forwardly jutting projections with a central cutout.

5. The cuvette of claim 4, wherein the central cutout has the shape of a notch.

6. The cuvette of claim 1, wherein the longitudinal axis extends through the drawing region.

7. The cuvette of claim 1, wherein the drawing center axis and the longitudinal axis at least approximately coincide.

8. The cuvette of claim 1, wherein the marginal regions run symmetrically in relation to the drawing center axis.

9. The cuvette of claim 8, wherein the marginal regions extend toward one another in a direction oblique in relation to the drawing center axis.

10. The cuvette of claim 1, wherein the marginal regions open into the end region.

11. The cuvette of claim 1, wherein the width of the marginal regions diminishes toward the end region.

12. The cuvette claim 1, wherein the marginal regions are rectilinear.

13. The cuvette of claim 1, wherein the end region adjoins the marginal regions in a manner extending transversely in relation thereto.

14. The cuvette of claim 1, wherein the end region is of curved form.

15. The cuvette of claim 14, wherein the end region has the shape of an arcuate portion.

16. The cuvette of claim 1, wherein the opening of the end region extends over the entire length of the end region.

17. The cuvette of claim 1, wherein the opening of the end region is formed in both wall surfaces that delimit the end region.

18. The cuvette of claim 1, wherein the wall surfaces defining the slot of the cavity extend into the end region, with wall portions that are reduced in height.

19. The cuvette of claim 18, wherein the wall portions have tapered edges.

20. The cuvette of claim 1, wherein the spacing between the delimiting surfaces of the marginal regions is at least 50 µm greater than the spacing between the adjacent parallel wall surfaces.

21. The cuvette of claim 20 wherein the spacing between the delimiting surfaces of the marginal regions is at least 100 µm greater than the spacing between the adjacent parallel wall surfaces.

* * * * *